(12) United States Patent
Jo et al.

(10) Patent No.: US 11,306,074 B2
(45) Date of Patent: Apr. 19, 2022

(54) CHEMICAL AND METHOD FOR ANALYZING DNA SEQUENCE BY VISUALIZING SINGLE-MOLECULE DNA AND USE THEREOF

(71) Applicant: SOGANG UNIVERSITY RESEARCH FOUNDATION, Seoul (KR)

(72) Inventors: Kyu Bong Jo, Seoul (KR); Seong Hyun Lee, Seoul (KR); Hiroshi Sugiyama, Kyoto (JP)

(73) Assignee: Sogang University Research Foundation, Seoul (KR)

( * ) Notice: Subject to any disclaimer, the term of this patent is extended or adjusted under 35 U.S.C. 154(b) by 251 days.

(21) Appl. No.: 16/446,887

(22) Filed: Jun. 20, 2019

(65) Prior Publication Data
US 2020/0031810 A1    Jan. 30, 2020

(30) Foreign Application Priority Data
Jul. 24, 2018    (KR) .................. 10-2018-0086255

(51) Int. Cl.
| | | |
|---|---|---|
| *C07D 405/14* | (2006.01) | |
| *C12Q 1/68* | (2018.01) | |
| *C12Q 1/6806* | (2018.01) | |

(52) U.S. Cl.
CPC ......... *C07D 405/14* (2013.01); *C12Q 1/6806* (2013.01); *C12Q 2563/107* (2013.01)

(58) Field of Classification Search
CPC .. C07D 403/02; C07D 403/12; C07D 403/14; C07D 405/14; C07D 404/14; C12Q 1/6806
See application file for complete search history.

(56) References Cited

FOREIGN PATENT DOCUMENTS

| | | |
|---|---|---|
| KR | 20160115553 A | 10/2016 |
| KR | 10-2018-0001712 A | 1/2018 |

OTHER PUBLICATIONS

Yusuke Kawamoto et al. J. Am. Chem. Soc. 2016, 138, 14100-14107 (Year: 2016).*
Lee et al. Nucleic Acids Research, 2018, vol. 46, No. 18, e108, pp. 1-9.(available online Jun. 21, 2018) (Year: 2018).*
Notice of Allowance dated May 27, 2020 for Korean Patent Application No. 10-2018-0086255, Cho et al., "Chemicals and Method for Analyzing DNA Sequences by Visualizing Single-molecule DNA," filed Jul. 24, 2018 (6 pages).
Nishijima et al., "Cell permeability of Py-Im-polyamide-fluorescein conjugates: Influence of molecular size and Py/Im content," Bioorg. Med. Chem. 18(2):978-983 (2010).
Notification of Reasons for Refusal of Korean Application No. 10-2018-0086255, dated Nov. 20, 2019 (7 pages).

* cited by examiner

*Primary Examiner* — Jezia Riley
(74) *Attorney, Agent, or Firm* — Clark & Elbing LLP; Susan M. Michaud

(57) ABSTRACT

The present disclosure relates to a composition for analysis of DNA sequences and a method for analysis of DNA sequences by using the same and, more particularly, to a composition comprising the compound represented by Chemical Formula 1 and a method for analysis of DNA sequences, the method comprising a step of treating a sample with the same. The compound represented by Chemical Formula 1 in which TAMRA is linked to polypyrrole specifically binds an A/T base pair (W) to fluoresce alone without causing DNA photocleavage. Therefore, the compound is useful for DNA analysis particularly at the single DNA molecule level.

10 Claims, 9 Drawing Sheets

CHEMICAL AND METHOD FOR ANALYZING DNA SEQUENCE BY VISUALIZING SINGLE-MOLECULE DNA AND USE THEREOF

TECHNICAL FIELD

The present disclosure relates to a composition for analysis of DNA sequences and a method for analysis of DNA sequences by using the same and, more particularly, to a composition comprising the compound represented by Chemical Formula 1 and a method for analysis of DNA sequences, the method comprising a step of treating a sample with the same.

The present patent application claims priority to and the benefit of Korean Patent Application No. 10-2018-0086255 filed in the Korean Intellectual Property Office on Jul. 24, 2018, the entire contents of which are incorporated herein by reference.

BACKGROUND ART

Direct visualization of individual DNA molecules is very important because it allows for understanding biochemical events within the context of DNA sequences. Although sequencing technology at the single nucleotide level has advanced, biological problems still remain unsolved, which are limited by short read length and information loss within a large genome.

The ultimate goal of DNA analysis would be to acquire nucleotide sequences and epigenetic information directly from chromosomal DNA without fragmentation or amplification. Given these concerns, single DNA molecules are a promising platform to overcome limitations of current sequencing technology.

In this regard, optical mapping, which is a technique for gaining genetic information by visualizing a large DNA molecule, has been continually developed. This technique is a method to make barcode-like patterns from a single DNA molecule for visualization.

Meanwhile, conventional analysis methods using sequence-specific restriction enzymes retain the fundamental problem of DNA cleavage. Analysis methods using sequence-specific substances for A/T base pairs (Netropsin, etc.) and fluorescent dye markers raises the problem that YOYO-1, used as the fluorescent dye, causes light-induced DNA cleavage.

There is therefore a need for the development of a substance that can bind in a sequence-specific manner and fluoresce alone without causing DNA cleavage.

DETAILED DESCRIPTION OF THE INVENTION

Technical Problem

The present inventors endeavored to develop a composition capable of binding in a sequence-specific manner without DNA cleavage, and as a result, the present inventors confirmed that TAMRA-linked polypyrrole can bind specifically to A/T base pairs (W) and fluoresce alone without DNA photocleavage, and thus the present inventors completed the present invention.

Therefore, a purpose of the present disclosure is to provide a composition for analysis of DNA sequences, the composition comprising a compound represented by Chemical Formula 1.

Another purpose of the present discloses is to provide a method for analysis of DNA sequences, the method comprising a step of applying a DNA sequencing composition comprising a compound represented by Chemical Formula 1.

Technical Solution

The present inventors endeavored to develop a composition capable of binding in a sequence-specific manner without DNA cleavage, and as a result, the present inventors confirmed that TAMRA-linked polypyrrole can bind specifically to A/T base pairs (W) and fluoresce alone without DNA photocleavage.

The present disclosure pertains to a composition for analysis of DNA sequences, the composition comprising a compound represented by Chemical Formula 1 and a method for analysis of DNA sequences, the method comprising a step of treating a sample therewith.

Below, a detailed description will be given of the present disclosure.

In accordance with an aspect of the present invention, there is provided a composition for analysis of DNA sequences, the composition comprising a compound represented by the following Chemical Formula 1:

[Chemical Formula 1]

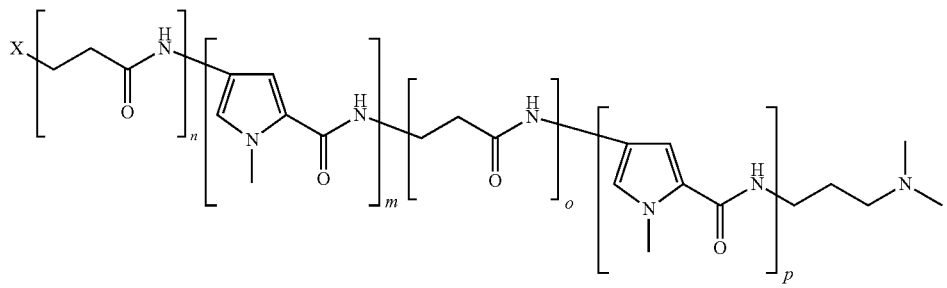

wherein, n, m, o, and p are each independently an integer of 1 to 10, and

X may be a fluorescent protein, a photoprotein, a color reaction-catalyst, biotin, a fluorescent substance, a luminescent substance, or a chemiluminescent substance.

The color reaction-catalyst may be, but not limited to, alkaline phosphatase, peroxidase, β-galactosidase, and/or β-glucosidase.

The fluorescent substance may be, but not limited to, TAMRA (carboxytetramethylrhodamine), fluorescein), Cy5 (Cyanine 5), Cy3 (Cyanine 3), HEX (5'-Hexachloro-Fluorescein), TET (5'-Tetrachloro-Fluorescein), Dabsyl (4-(dimethylaminoazo) benzene-4-carboxylic acid), and/or FAM (Fluorescein amidite).

In Chemical Formula 1, n, m, o, and p may each be independently an integer of 1 to 5.

In Chemical Formula 1, X may be as follows:

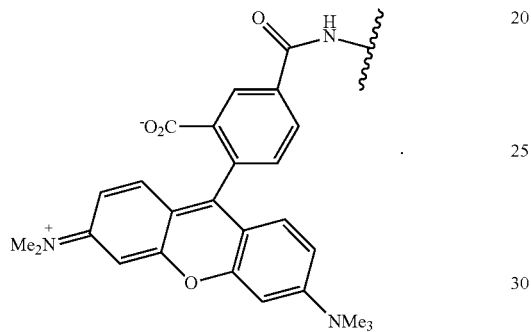

In addition, the compound represented by Chemical Formula 1 may be a compound represented by the following Chemical Formula 2:

[Chemical Formula 2]

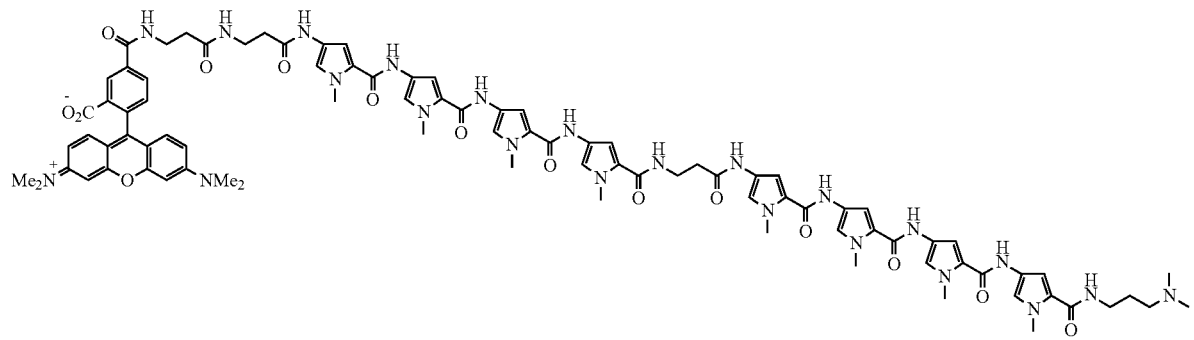

The composition may bind specifically to an adenine/thymine (A/T) base pair (W).

The DNA may be, but not limited to, a single DNA molecule, a chromosome, or a chromatin fiber.

The composition binds DNA via a hydrogen bonding interaction between a polypyrrole and the minor-groove of DNA while the TAMRA (carboxytetramethylrhodamine) moiety remains far from the DNA backbone. Thus, the composition has the advantage of suppressing the DNA photocleavage, which is a significant problem with the conventional DNA dye YOYO-1 and thus does not cleave DNA during repeated cycles of DNA elongation and relaxation.

Moreover, the composition can analyze chemically modified or damaged DNA sequences or backbones, unlike typical sequencing approaches, and can be, thus, effectively used at the single DNA molecule level.

In accordance with another aspect of the present invention, there is provided a method for analysis of DNA sequences comprising: a step of treating a sample with a compound represented by the Chemical Formula 1:

[Chemical Formula 1]

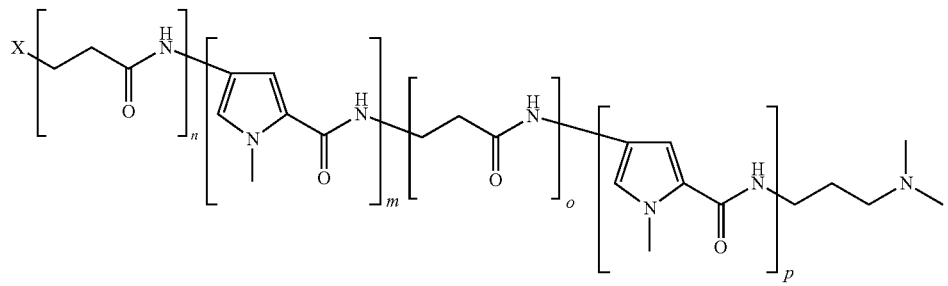

wherein, n, m, o, and p are each independently an integer of 1 to 10,

X may be a fluorescent protein, a photoprotein, a color reaction-catalyst, biotin, a fluorescent substance, a luminescent substance, or a chemiluminescent substance.

The method may further comprise: a step of comparing an entire genomic adenine/thymine (A/T) frequency in a subject to be analyzed and an A/T frequency of the sample treated with the composition.

The composition may specifically bind to an adenine/thymine (A/T) base pair (W).

The sample may be, but not limited to, a genetic material comprising a single DNA molecule, an oligo DNA, a chromosome, a polytene chromosome, or a chromatin fiber.

In the method, a target DNA sequence may be analyzed using, for example, a Python program in which the entire genomic A/T frequency of a subject to be analyzed is scanned through in silico map and a search is made of the best alignment position between the image of the sample treated with the composition and the scanned entire genomic A/T frequency.

The overlapping description of the composition is omitted in consideration of the complexity of the specification.

Advantageous Effects

The present invention is directed a composition for analysis of DNA sequences and a method for analysis of DNA sequences by using the same and, more particularly, to a composition comprising the compound represented by Chemical Formula 1 and a method for analysis of DNA sequences, the method comprising a step of treating a sample with the same.

The compound of the present disclosure, represented by Chemical Formula 1, in which TAMRA is linked to a polypyrrole, specifically binds an A/T base pair (W) to fluoresce alone, without DNA photocleavage and can be thus useful particularly for DNA analysis.

DETAILED DESCRIPTION OF THE EXEMPLARY EMBODIMENTS

Figure 1:
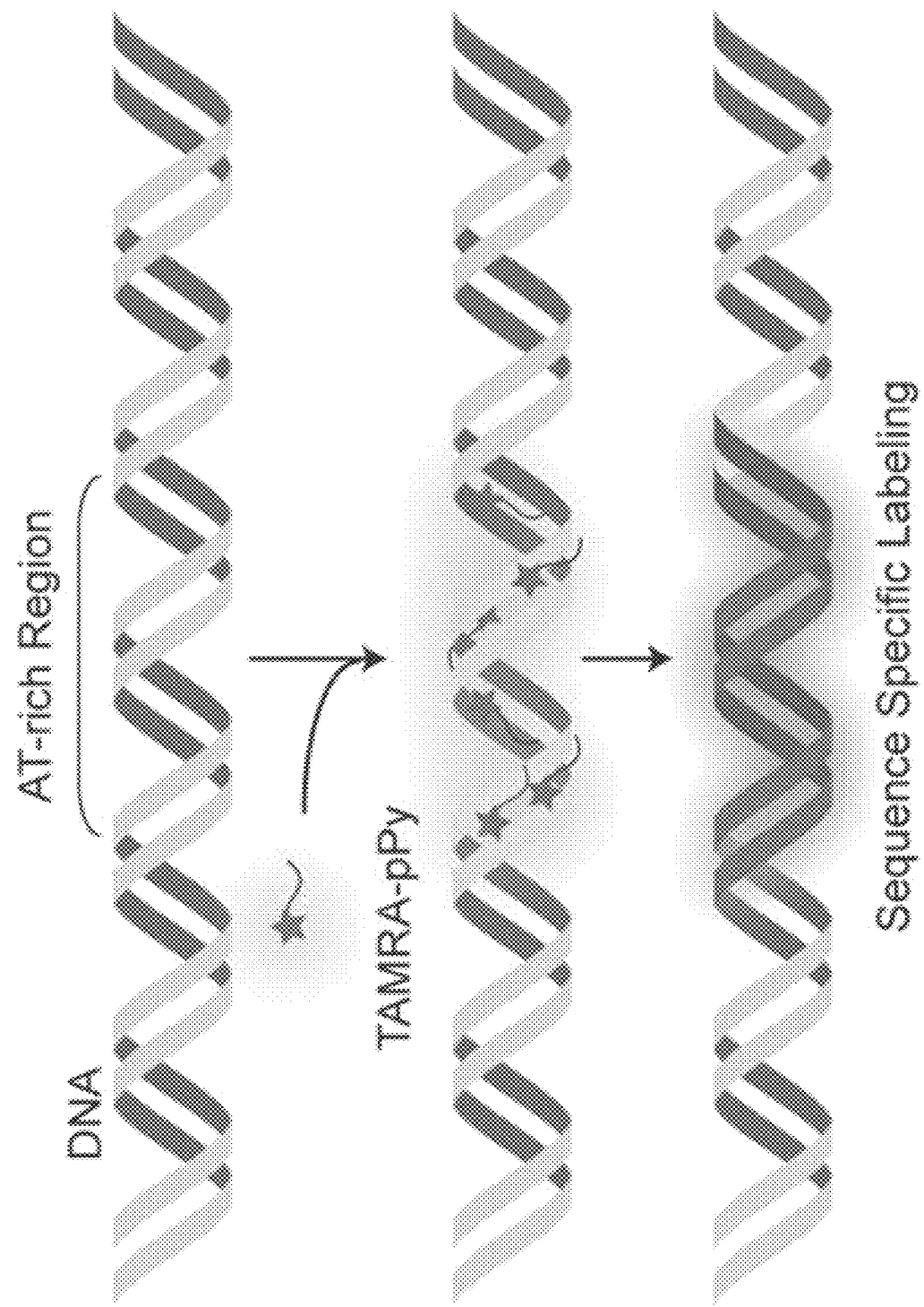
FIG. 1 is a schematic illustration of a DNA molecule stained specifically at adenine (A) and thymine (T) rich regions according to an embodiment of the present disclosure.

Hereinafter, the present invention will be described in further detail with reference to examples. It is to be understood, however, that these examples are for illustrative purposes only and are not to be construed to limit the scope of the present invention.

Preparation Example: Preparation of TAMRA-$\beta_2$-$Py_4$-$\beta$-$Py_4$-Dp

Fmoc-Py-COOH, an oxime resin, HCTU, DIEA, and dimethylformamide (DMF) were used to afford 50 mg of an Fmoc-Py-oxime resin (0.40 mmol/g).

Briefly, 20% piperidine/DMF (500 μL) was deblocked twice for 4 minutes, and 10% DIEA/N-methyl pyrrolidone (NMP) (364 μL, 0.21 mmol DIEA) was added to an Fmoc-Py-COOH (77 mg, 0.21 mmol) or Fmoc-β-COOH (66 mg, 0.21 mmol)-HCTU mixture, followed by a coupling reaction for 60 minutes (sequentially, four times with Fmoc-Py-COOH, once with Fmoc-β-COOH, four times with Fmoc-Py-COOH, and twice with Fmoc-β-COOH). The reaction mixture was washed five times with DMF after each step. After the last coupling reaction, the amino group at the N-terminus was deprotected. All coupling reactions were carried out with a single-coupling cycle. All lines were purged with solution and bubbled by nitrogen gas for stirring the resin.

Subsequently, polypyrrole on the resin was cleaved with 0.60-1.0 mL of N, N-dimethyl-1,3-propanediamine or 3,3'-diamino-N-methyldipropylamine at 55° C. for 3 hours. The resin was removed by filtration and washed thoroughly with dichloromethane, and the filtrate was concentrated in a vacuum. The residue was dissolved in 1.0 to 2.0 mL of a dichloromethane-methanol mixture and then more than 10-fold volumes of diethyl ether was added, followed by centrifugation at 10,000×g for 10 minutes and removal of the supernatant. This process was repeated until while precipitates were obtained.

The crude product thus obtained was purified by reversed-phase flash chromatography (CombiFlash Rf, Teledyne Isco, Lincoln, Nebr.) using a 4.3 g reversed-phase flash column (C18 RediSep Rf) in 0.1% TFA (in water) with acetonitrile serving as an eluent. Collected fractions were lyophilized to obtain $H_2N$-β-alanine)$_2$-(N-methylpyrrole)$_4$-(β-alanine)-(N-methylpyrrole)$_4$-(3-(dimethylamino)propylamine) ($H_2N$-β$_2$-Py$_4$-β-Py$_4$-Dp) (19 mg, $1.5 \times 10^{-2}$ mmol).

Afterward, $H_2N$-β$_2$-Py$_4$-β-Py$_4$-Dp (1.3 mg, $1.0 \times 10^{-3}$ mmol) obtained above and 5-TAMRA NHS ester (1.2 mg, $2.3 \times 10^{-3}$ mmol) were dissolved in DMF (190 μL) and DIEA (0.70 μL, $4.0 \times 10^{-3}$ mmol) and then mixed at room temperature, with light shielded therefrom. The reaction mixture was purified by reversed-phase high performance liquid chromatography (HPLC), followed by lyophilization to afford (5-carboxytetramethylrhodamine)-(β-alanine)$_2$-(N-methylpyrrole)$_4$-(β-alanine)-(N-methylpyrrole)$_4$-(3-(dimethylamino)propylamine) (TAMRA-β$_2$-Py$_4$-β-Py$_4$-Dp) as a purple powder (1.7 mg, $1.0 \times 10^{-3}$ mmol, quant).

HPLC: $t_R$=18.2 min. MALDI-TOF-MS m/z calcd for $C_{87}H_{98}N_{23}O_{15}^+$[M+H]$^+$ 1704.761 found 1704.766.

Comparative Example 1: Preparation of TAMRA-β$_2$-Py$_4$-Dp $H_2N$-β$_2$-Py$_4$-Dp was prepared in the same manner as in the Preparation Example, with the exception of using 100 mg of an Fmoc-Py-oxime resin (0.36 mmol/g) according to the different number of the coupling reactions of Fmoc-Py-COOH or Fmoc-β-COOH (sequentially, twice with Fmoc-β-COOH and four times with Fmoc-Py-COOH).

Afterwards, $H_2N$-β$_2$-Py$_4$-Dp (1.1 mg, $1.5 \times 10^{-3}$ mmol) was dissolved in DMF (140 μL) and DIEA (0.52 μL, $3.0 \times 10^{-3}$ mmol) and mixed at room temperature, with light shielded therefrom. The reaction mixture was purified by reversed-phase high-performance liquid chromatography, followed by lyophilization to afford (5-carboxytetramethylrhodamine)-(β-alanine)$_2$-(N-methylpyrrole)$_4$-(3-(dimethylamino)propylamine)(TAMRA-β$_2$-Py$_4$-Dp) as a purple powder (1.5 mg, $1.3 \times 10^{-3}$ mmol).

HPLC: $t_R$=17.2 min. MALDI-TOF-MS m/z calcd for $C_{60}H_{69}N_{14}O_{10}^+$[M+H]$^+$ 1145.532 found 1145.559.

Comparative Example 2: Preparation of TAMRA-β$_2$-Py$_4$-TAMRA $H_2N$-β$_2$-Py$_4$-NH$_2$ was prepared in the same manner as in the Preparation Example, with the exception of using 85 mg of an Fmoc-Py-oxime resin (0.27 mmol/g) according to the different number of the coupling reactions of Fmoc-Py-COOH or Fmoc-β-COOH (sequentially, twice with Fmoc-β-COOH and four times with Fmoc-Py-COOH).

Afterward, $H_2N$-β$_2$-Py$_4$-NH$_2$ (2.3 mg, $3.0 \times 10^{-3}$ mmol) and 5-TAMRA NHS ester (3.1 mg, $5.9 \times 10^{-3}$ mmol) were dissolved in DMF (200 μL) and DIEA (10 μL, $5.7 \times 10^{-2}$ mmol) and mixed at room temperature, with light shielded therefrom. The reaction mixture was purified by reversed-phase high-performance liquid chromatography, followed by lyophilization to afford (5-carboxytetramethylrhodamine)-(β-alanine)$_2$-(N-methylpyrrole)$_4$-(5-carboxytetramethylrhodamine)(TAMRA-β$_2$-Py$_4$-TAMRA) as a purple powder (1.2 mg, $7.5 \times 10^{-4}$ mmol).

HPLC: $t_R$=18.2 min. MALDI-TOF-MS m/z calcd for $C_{87}H_{94}N_{17}O_{14}^+$[M+H]$^+$ 1600.716 found 1600.779.

Fluorescence Microscopy and DNA Visualization

An inverted microscope (Olympus IX70, Tokyo, Japan) with 60× Olympus UPlanSApo oil immersion objectives illuminated with an LED light source (SOLA SM II light engine, Lumencor, Beaverton, Oreg., USA) was used. The light was passed through corresponding filter sets (Semrock, Rochester, N.Y., USA) to set the excitation and emission wavelengths. A maximum light intensity of 140 mW/cm$^2$ was measured. Fluorescence microscopic images were taken with an electron-multiplying charge-coupled device digital camera (Evolve EMCCD, Roper Scientific, Tucson, Ariz., USA) and stored in a 16-bit TIFF format using the software Micro-manager. For image processing and analysis, ImageJ software with Java plug-ins and python programs developed by the present inventors were utilized.

Python Program

ImageCompare.py: a library of functions, seq2map.py: to convert a FASTA file into a A/T frequency in silico map wherein a selected sequence is represented in white for high frequency regions and in black for low frequency regions.

insilicoMapFolder.py: to scan and compare in silico image files and DNA images obtained through experiments with respect to all images in the folder, to search positions of sites having the highest cross-correlation coefficient, to convert the values, and to store the values in new record files.

sortView.py: to read record files obtained with the insilicoMapFolder.py, to compare signals, to search cross-correlation coefficients, and to visualize image comparison in a new window.

randomtiff.py: to generate random intensity tiff images

Experimental Example 1: Identification of DNA Staining at Single Molecule Level

First, λ DNA (NCBI: NC_001416.1) was diluted to a concentration of 5 ng/μL (0.16 nM; base pair 7.76 μM) in 1×TE (10 mM Tris, 1 mM EDTA, pH 8.0) and mixed at a volume ratio of 1:1 with 70 μM of the Preparation Example solution. Next, the mixture was incubated at room temperature for 15 min and 20-fold diluted with 4% 3-mercaptoethanol (β-ME) in 1×TE.

Separately, a flow chamber (5×10×0.1 mm (L×W×H)) was prepared by placing an acrylic support on an acid-cleaned cover slip, with the walls formed by double-sided tape, An NE-1000 syringe pump (New Era Pump Systems Inc., Wantagh, N.Y.) was used to control the buffer.

Thereafter, 40 μg/mL biotinylated bovine serum albumin (BSA) was injected and incubated at room temperature for 10 min, after which a dilution of 20 μg/mL Neutravidin in T50 solution (10 mM Tris, 50 nM NaCl, pH 8.0) was injected to the flow chamber and incubated at room temperature for 10 min.

Then, 1 μM of λ DNA overhang oligo (5'-p-GGGCGGCGACCT-Triethyleneglycol-biotin-3') was loaded into the flow chamber and maintained at room temperature for 10 minutes. λ DNA, 200 U of T4 DNA ligase, and reaction buffer were added and incubated at room temperature for 30 minutes.

After the residual enzyme mixture was washed with 1×TE, the diluted Preparation Example solution was flowed into the channels, resulting in visualization of the tethered DNA. Stained DNA molecules were visualized under a continuous flow of 1×TE (100 μl/minute).

Figure 2A:
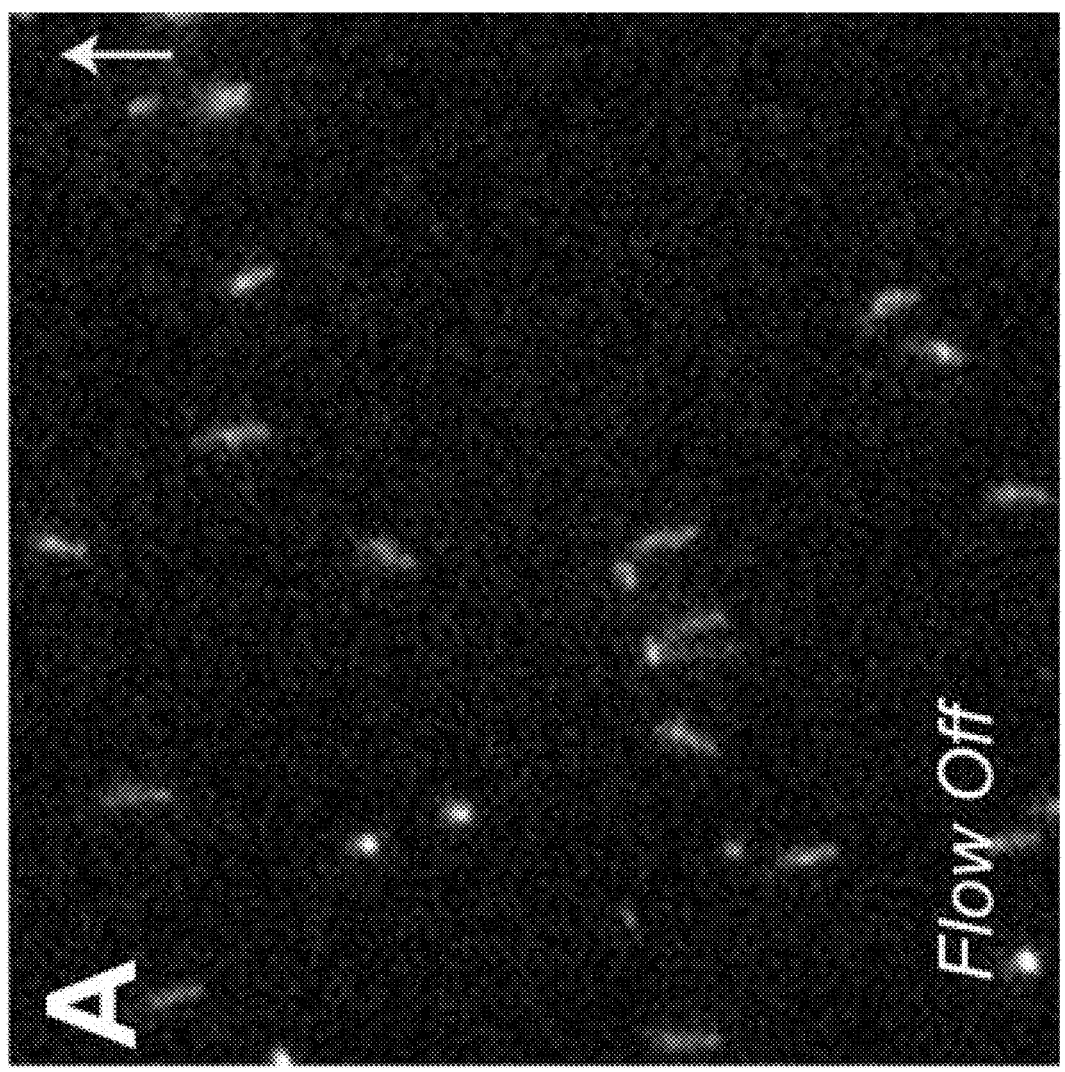
FIG. 2a is a view of λ DNA (48.5 kbp) molecules stained according to an embodiment of the present disclosure that have a mushroom-like conformation in the flow off condition.
Figure 2B:
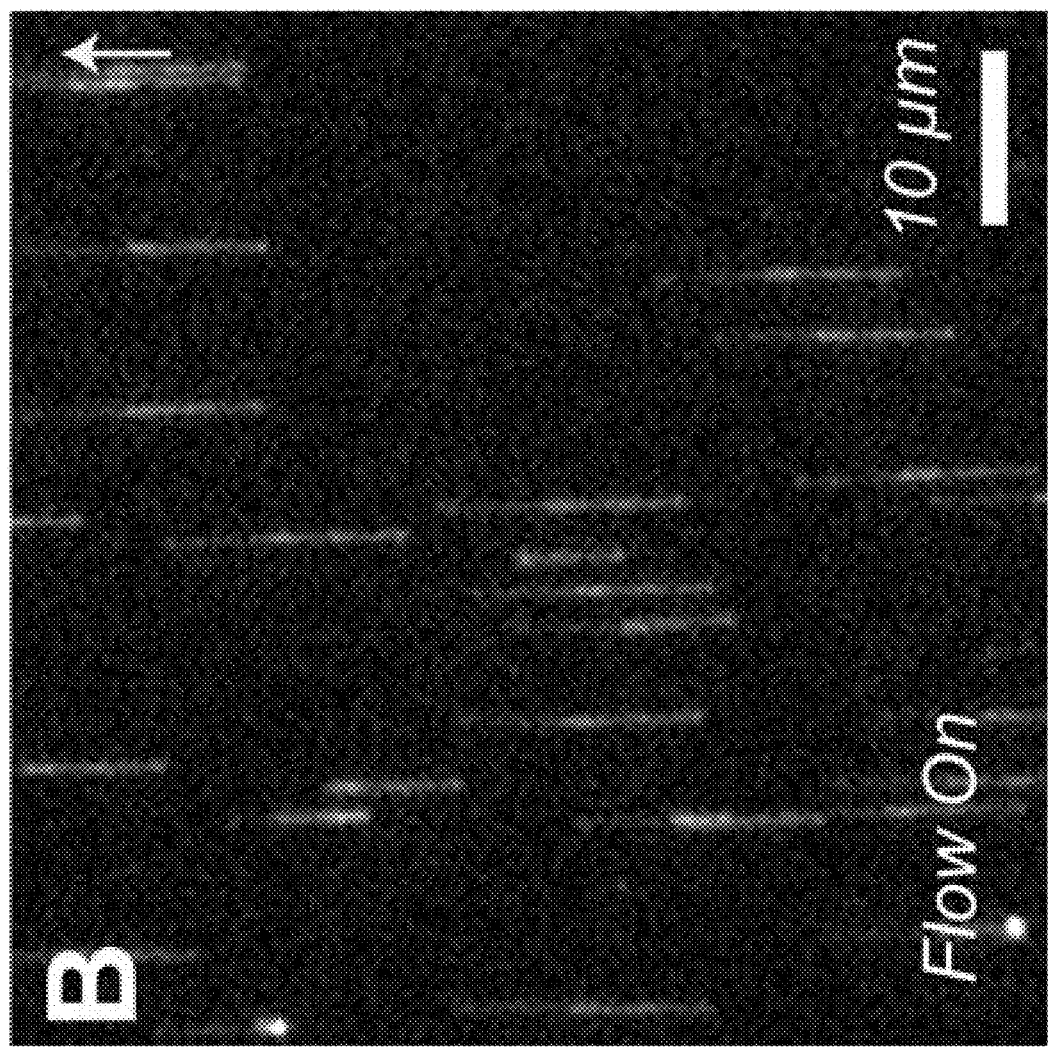
FIG. 2b is a view of λ DNA molecules stained according to an embodiment of the present invention that are fully elongated in a 100 μL/min flow condition.
Figure 2C:
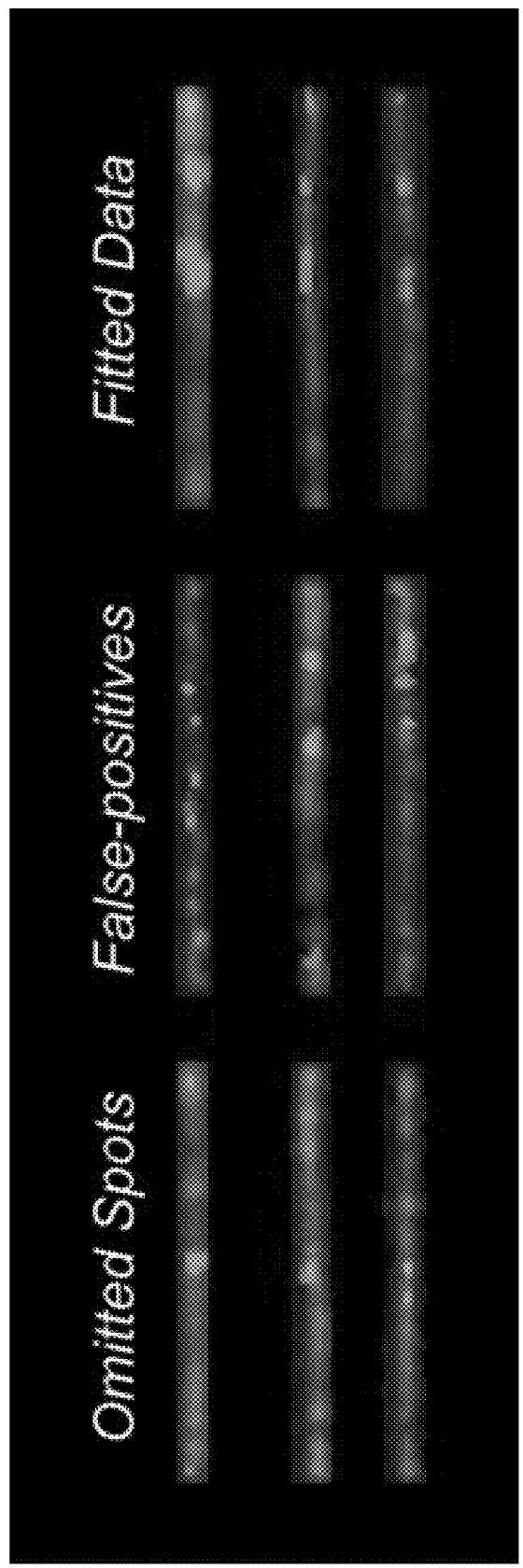
FIG. 2c is a view of false-labeled DNA molecules stained according to a Comparative Example.

As shown in FIGS. 2a to 2c, the compound of the Preparation Example visualized λ DNA molecules with sequence specificity as well as enhancing the intensity of the molecules. The λ DNA molecules stained with the compound of the Preparation Example were free-floating with a mushroom-like conformation (FIG. 2a) and were fully elongated at a flow of 100 μL/minute (FIG. 2b).

In contrast, the compound of Comparative Example 1 stained only in part AT-rich regions and bound undesired regions. The images were not bright enough to efficiently visualize the DNA backbone (FIG. 2c). In addition, the compound of Comparative Example 2 did not bind double-stranded DNA at all, resulting in no observation of fluorescence, probably because the steric hindrance of two TAMARAs at both ends inhibited tetra-pyrrole (Py$_4$) binding to DNA.

Experimental Example 2: Identification of DNA Binding at Single Molecule Level

The tethering possibility of the compound of the Preparation Example to three candidates (W, W$_4$, and W$_9$) as binding sequences was identified as follows: 1) the compound binds nine consecutive A/T base pairs (W$_9$); 2) tetra-pyrrole (Py$_4$) binds four consecutive A/T base pairs and the other works as a linker (W$_4$); and 3) the compound randomly interacts with one A/T (W) rather than consecutive sequences.

Cross-correlation (cc) coefficient values calculated by comparing the alignment of 20 molecular images of above three kinds of binding sequences (W, W$_4$ and W$_9$) with the genome. The control cross-correlation coefficient (hereinafter referred to as cc) was obtained by comparing the 100 computer-generated random sequences with the in silico images (***P<0.0001 for random-sequences paired t-test).

$$\text{Cross-correlation coefficient}(r) = \frac{\sum_{i=1}^{n}(x_i - \tilde{x})(y_i - \tilde{y})}{\sqrt{\sum_{i=1}^{n}(x_i - \tilde{x})^2} \sqrt{\sum_{i=1}^{n}(y_i - \tilde{y})^2}}$$

($n$ = number of sample, $x_i$, $y_i$ = value at each site, $\bar{x}$, $\bar{y}$ = sample average)

Figure 3A:
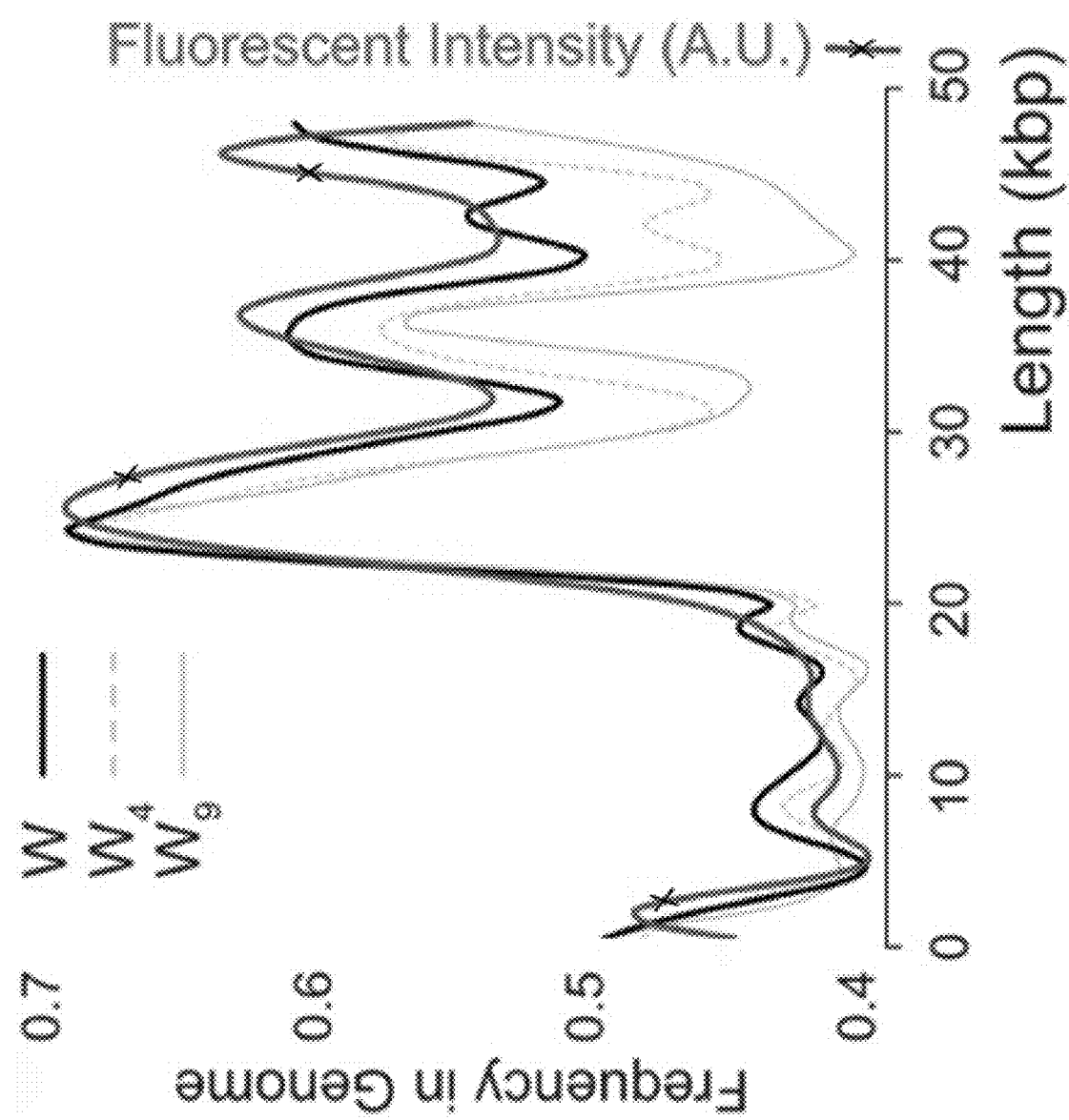
FIG. 3a is a view showing the comparison of experimentally measured fluorescence intensity with in silico sequence frequencies for genome sequences (W, $W_4$, and $W_9$) from the λ genome sequence stained according to an embodiment of the present disclosure.
Figure 3B:
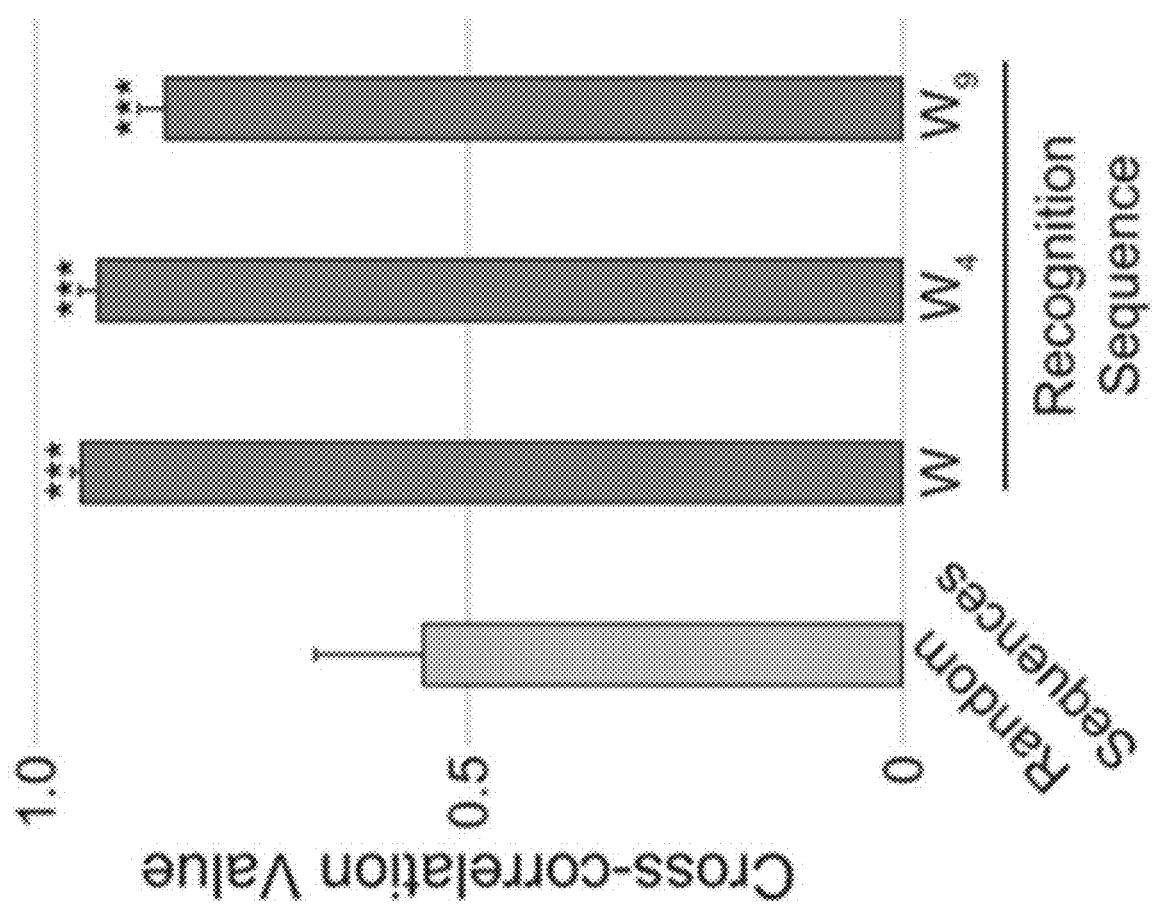
FIG. 3b is a view showing the comparison of cross-correlation coefficient values calculated from the alignment of 20 molecular images with the λ DNA genome.

As can be seen in FIGS. 3a and 3b, comparison was made between experimentally measured fluorescence intensity and the three fluorescence intensity profiles (FIG. 3a), indicating that the experimental measurement agrees better with simple A/T frequency than W$_4$ and W$_9$. In addition, cc was calculated using the Python program, showing the highest cc value for simple A/T frequency (FIG. 3b).

Experimental Example 3: Identification of DNA Staining-Induced DNA Photocleavage First, 1 μL of a λ DNA solution (500 ng/μL) was added to a restriction enzyme (HindIII) reaction solution to form a total reaction volume of 50 μL and the reaction was allowed to progress at 37° C. for 1 hour, followed by incubating at 65° C. for 15 minutes to inactivate the restriction enzyme digestion.

YOYO-1 stained DNA: YOYO-1 was mixed with 100 ng of the λ DNA to form a final concentration of 4 μM, followed by incubation at room temperature for 15 minutes. The mixture was exposed to 488 nm light source at room temperature for 30 minutes.

DNA stained with the compound of the Preparation Example: 100 ng of the λ DNA was mixed with the compound of the Preparation Example at a final concentration of 100 μM, followed by incubation at room temperature for 15 minutes. Exposure was made to 580 nm light for 30 minutes.

Control: a λ DNA solution containing no dyes and an unilluminated λ DNA solution were used.

Each of the solutions was electrophoresed for 30 minutes on 0.7% agarose gel and observed.

Figure 4:
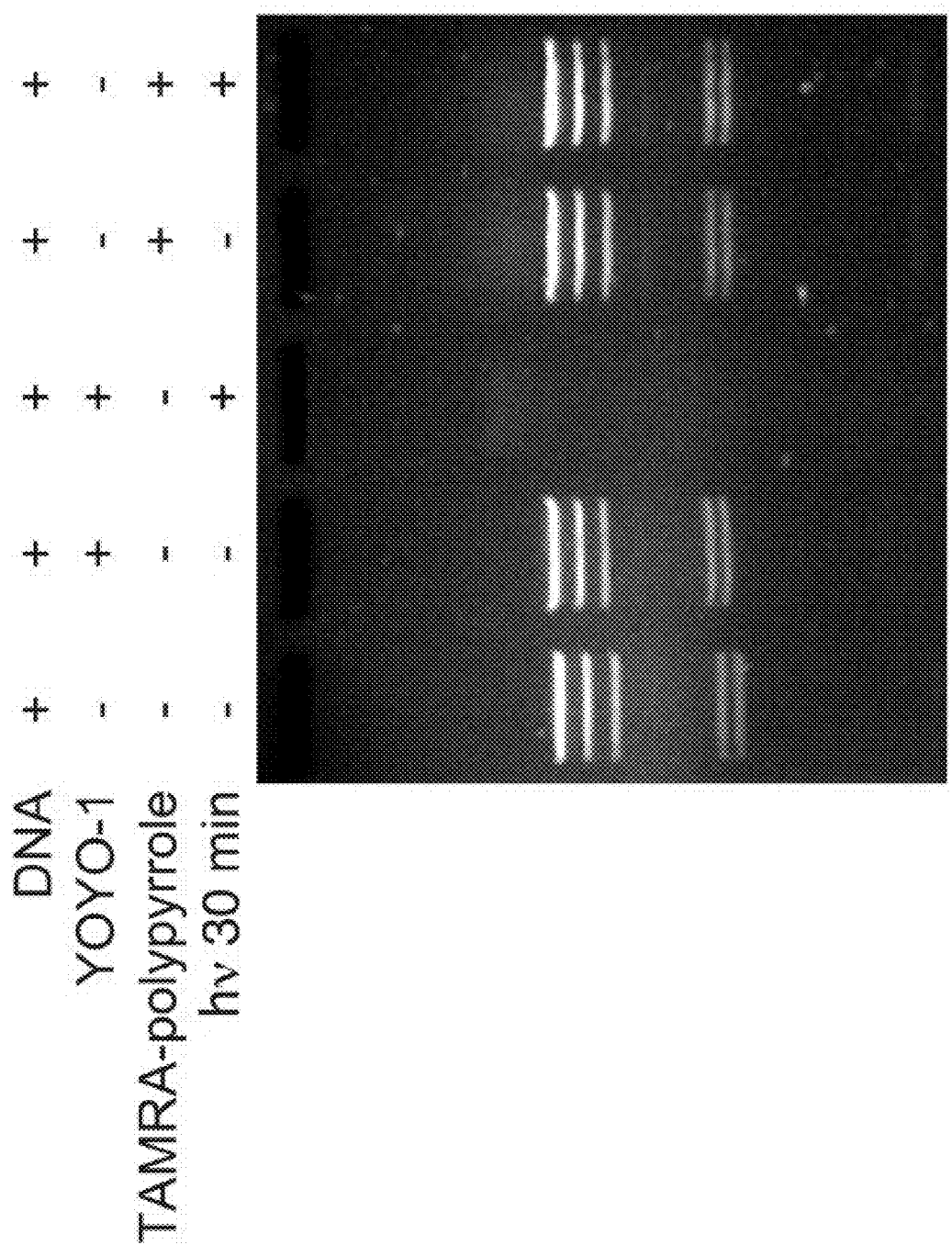
FIG. 4 shows photo-cleavage gel electrophoresis assay results of λ DNA stained with the compound according to an embodiment of the present disclosure and YOYO-1.

As can be seen in FIG. 4, YOYO-1-stained DNA completely disappeared whereas the DNA stained with the compound of the Preparation Example was not affected at all.

Experimental Example 4: Identification of DNA Staining at Chromosomal Level

For comparison with DAPI, which is conventionally used to visualize polytene chromosomes on a fluorescence microscope, the polytene chromosomes from the *Drosophila melanogaster* salivary gland were stained with the compound.

In brief, dissected salivary glands from third larvae of *Drosophila melanogaster* were fixed with a solution containing a 1:2:3 ratio of propionic acid, deionized water, and acetic acid on a positively charged coverslip. Then, the cells were located between a slide glass and the coverslip and then the individual cells were gently spread. After moving the coverslip back and forth on the slide glass, the spread cells were squashed for up to 15 minutes. Then, the slide glass and coverslip were slightly dipped into liquid nitrogen. Just after no more bubbles were generated, the cover slip was removed from the slide glass. Finally, a dilution of 2.5 μM of the compound of the Preparation Example in 4% β-ME was used to stain the polytene chromosomal DNA.

Figure 5A:
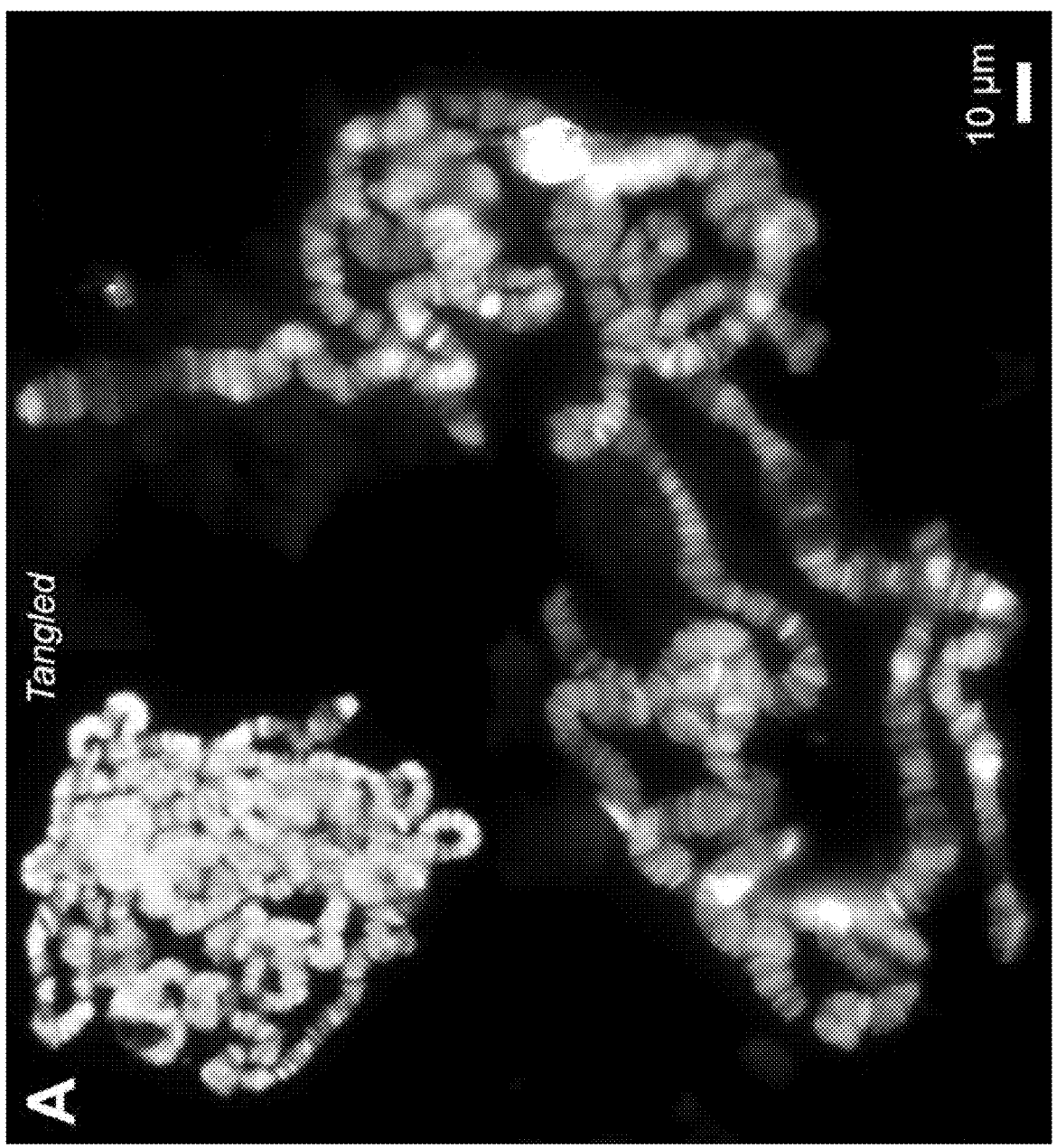
FIG. 5a shows images of tangled and spread polytene chromosomes from *D. melanogaster* after staining according to an embodiment of the present disclosure.
Figure 5B:
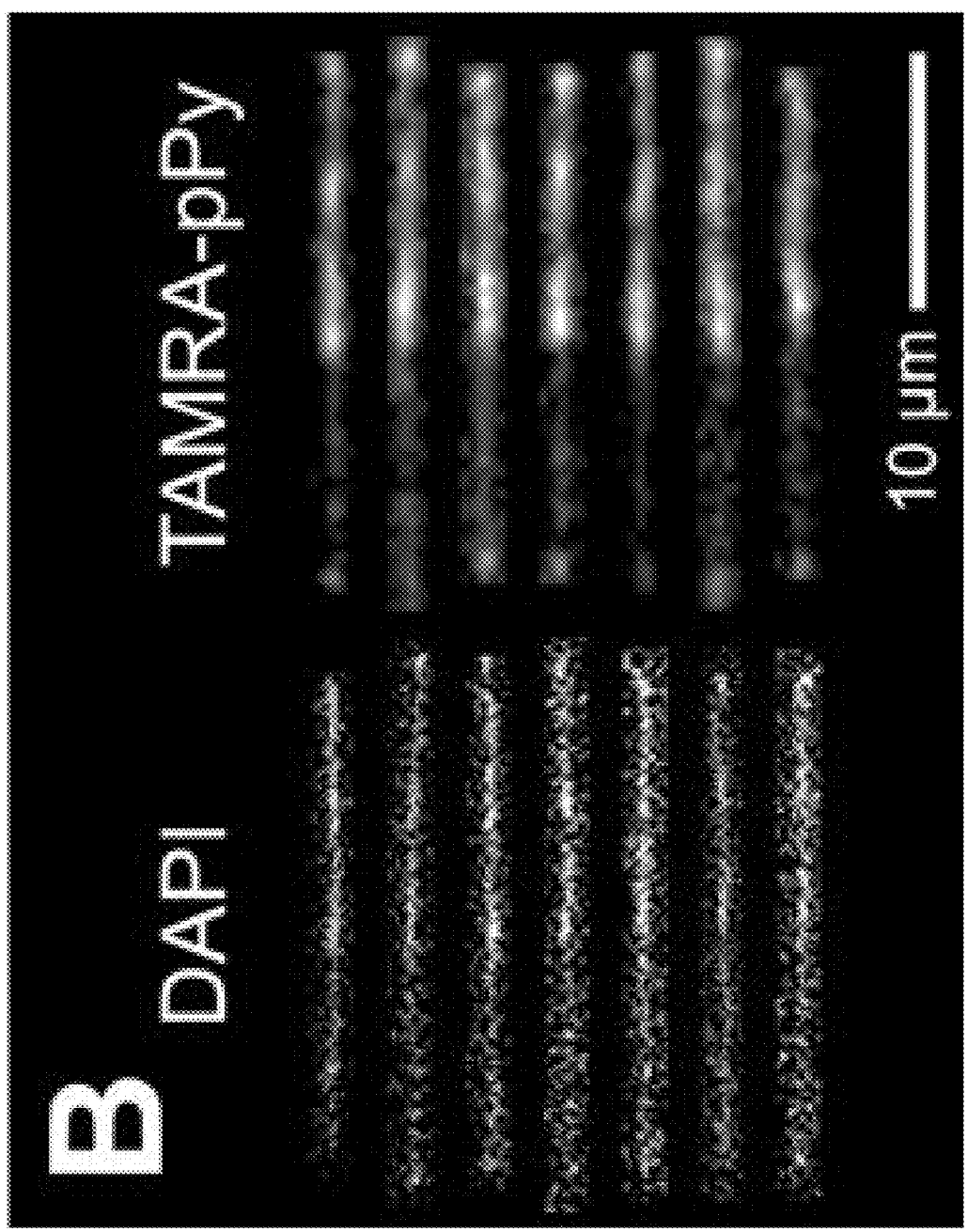
FIG. 5b shows fluorescent λ DNA images stained with the compound of an embodiment of the present disclosure and DAPI.

FIG. 5a shows a typical image for tangled and spread polytene chromosomes, both of which clearly demonstrate band and interband patterns. In addition, the DNA stained with the compound of the Preparation Example DNA exhibits a clear backbone compared with DAPI-stained DNA, as shown in FIG. 5b. The compound of the Preparation Example is excited by yellow wavelengths (580) and does not damage DNA, whereas DAPI require ultraviolet light sources or equivalent low wavelength light to excite the fluorophores, which can damage DNA.

CONCLUSION

Taken together, the data imply that the composition of the present invention specifically stains AT-rich regions in DNA and exhibits distinct fluorescence intensity patterns on DNA backbones when binding DNA. Moreover, such a sequence-specific pattern allows the determination of the DNA sequence from a microscopic image of a DNA fragment if given the full sequence. Therefore, the composition of the present invention can be effectively used for analyzing huge single DNA molecules at high speed and high yield.

Staining polytene chromosomal DNA with the composition of the present invention can exhibit the band and interband patterns with a high-resolution, so that the composition of the present invention is useful for studying somatic genome instability, chromosomal organization of the genome, and protein immunolocalization.

What is claimed is:

1. A composition for analysis of DNA sequences, the composition comprising a compound represented by the following Chemical Formula 1:
   wherein,
   n is an integer of 2 to 10, m, o, and p are each independently an integer of 1 to 10, and
   X is one selected from the group consisting of a fluorescent protein, a photoprotein, a color reaction-catalyst, biotin, a fluorescent substance, a luminescent substance, and a chemiluminescent substance.

2. The composition of claim 1, wherein the fluorescent substance is one selected from the group consisting of TAMRA (carboxytetramethylrhodamine), fluorescein, Cy5 (Cyanine 5), Cy3 (Cyanine 3), HEX (5'-hexachloro-fluorescein), TET (5'-tetrachloro-fluorescein), Dabsyl (4-(dimethylaminoazo)benzene-4-carboxylic acid), and FAM (fluorescein amidite).

3. The composition of claim 1, wherein n is an integer of 2 to 5; m, o, and p are each independently an integer of 1 to 5; and
X is

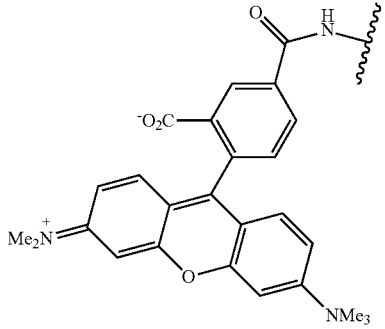

4. The composition of claim 1, wherein the compound represented by Chemical Formula 1 is a compound represented by the following Chemical Formula 2:

[Chemical Formula 2]

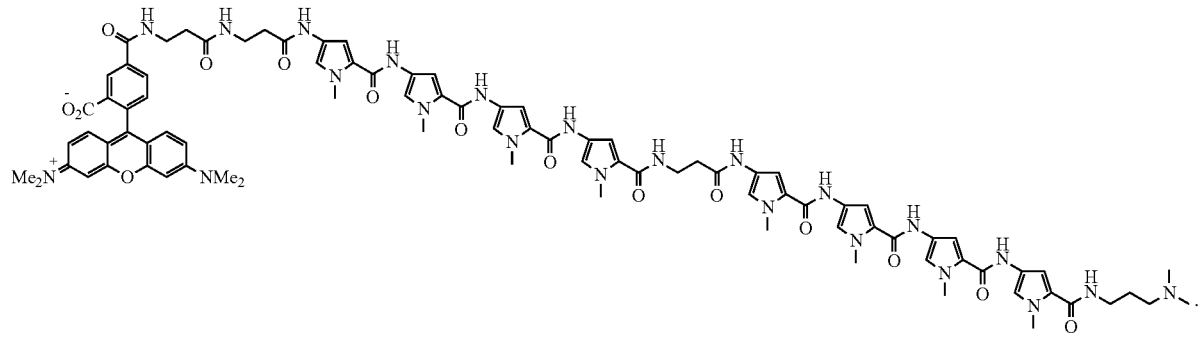

5. The composition of claim 1, binding to an adenine/thymine (A/T) base pair (W).

6. The composition of claim 1, wherein the DNA is one selected from the group consisting of a single DNA molecule, a chromosome, and a chromatin fiber.

7. A method for analysis of DNA sequences comprising:
a step of treating a sample with the composition of claim 1.

8. The method of claim 7, further comprising:
a step of comparing an entire genomic adenine/thymine (A/T) frequency in a subject to be analyzed and an NT frequency of the sample treated with the composition.

9. The method of claim 7, wherein the composition binds to an A/T base pair (W).

10. The method of claim 7, wherein the sample is at least one selected from the group consisting of a single DNA molecule, an oligo-DNA, a chromosome, a polytene chromosome, and a chromatin fiber.

\* \* \* \* \*